(12) United States Patent
Batista

(10) Patent No.: US 12,059,523 B2
(45) Date of Patent: Aug. 13, 2024

(54) AEROSOL GENERATING DEVICE COMPRISING SEMICONDUCTOR HEATERS

(71) Applicant: Altria Client Services LLC, Richmond, VA (US)

(72) Inventor: Rui Nuno Batista, Morges (CH)

(73) Assignee: Altria Client Services LLC, Richmond, VA (US)

( * ) Notice: Subject to any disclaimer, the term of this patent is extended or adjusted under 35 U.S.C. 154(b) by 0 days.

(21) Appl. No.: 18/056,007

(22) Filed: Nov. 16, 2022

(65) Prior Publication Data
US 2023/0071524 A1  Mar. 9, 2023

Related U.S. Application Data

(63) Continuation of application No. 16/835,988, filed on Mar. 31, 2020, now Pat. No. 11,533,786, which is a
(Continued)

(30) Foreign Application Priority Data

Apr. 22, 2016 (EP) .................................. 16166728

(51) Int. Cl.
*A61M 11/04* (2006.01)
*A24D 1/20* (2020.01)
(Continued)

(52) U.S. Cl.
CPC ........... *A61M 11/042* (2014.02); *A24F 40/46* (2020.01); *A24F 40/50* (2020.01); *A24F 40/51* (2020.01);
(Continued)

(58) Field of Classification Search
CPC ....... A61M 11/042; A24F 40/53; A24F 40/46; A24F 40/51; A24F 40/50; A24F 40/20;
(Continued)

(56) References Cited

U.S. PATENT DOCUMENTS 5,224,498 A   7/1993 Deevi et al.
5,530,225 A   6/1996 Hajaligol
(Continued)

FOREIGN PATENT DOCUMENTS

CN   201379072 Y   1/2010
CN   204682534 U   10/2015
(Continued)

OTHER PUBLICATIONS

European Search Report 16166728.2 dated Jun. 24, 2016.
(Continued)

*Primary Examiner* — Brian W Jennison
(74) *Attorney, Agent, or Firm* — Harness, Dickey & Pierce, P.L.C.

(57) ABSTRACT

An aerosol-generating device includes an electrical power supply, a cavity structure configured to receive an aerosol-generating article, and a plurality of semiconductor heaters within the cavity structure. Each of the plurality of semiconductor heaters includes a substrate layer and a heating layer on the substrate layer. The heating layer is a continuous layer. The aerosol-generating device includes a controller configured to control a supply of electrical power from the electrical power supply to each of the plurality of semiconductor heaters.

15 Claims, 3 Drawing Sheets

Related U.S. Application Data continuation of application No. 15/493,821, filed on Apr. 21, 2017, now Pat. No. 10,645,972, which is a continuation of application No. PCT/EP2017/057527, filed on Mar. 30, 2017.

(51) Int. Cl.

| | | |
|---|---|---|
| *A24F 40/20* | (2020.01) | |
| *A24F 40/46* | (2020.01) | |
| *A24F 40/50* | (2020.01) | |
| *A24F 40/51* | (2020.01) | |
| *A24F 40/53* | (2020.01) | |
| *G01N 27/14* | (2006.01) | |
| *G01N 33/00* | (2006.01) | |
| *H05B 1/02* | (2006.01) | |
| *H05B 3/26* | (2006.01) | |

(52) U.S. Cl.
CPC ......... *A24F 40/53* (2020.01); *G01N 33/0036* (2013.01); *H05B 1/0244* (2013.01); *H05B 3/26* (2013.01); *A24D 1/20* (2020.01); *A24F 40/20* (2020.01); *G01N 27/14* (2013.01); *H05B 2203/021* (2013.01); *Y02A 50/20* (2018.01)

(58) Field of Classification Search
CPC .. H05B 1/0244; H05B 3/26; H05B 2203/021; A24D 1/20
See application file for complete search history.

(56) References Cited

U.S. PATENT DOCUMENTS

| | | | |
|---|---|---|---|
| 2005/0233459 A1 | 10/2005 | Melker et al. | |
| 2013/0255702 A1 | 10/2013 | Griffith, Jr. et al. | |
| 2014/0060554 A1* | 3/2014 | Collett | A24F 40/46 |
| | | | 392/386 |
| 2014/0124783 A1* | 5/2014 | Kishida | H01L 27/1225 |
| | | | 257/66 |
| 2014/0216450 A1* | 8/2014 | Liu | A24F 40/40 |
| | | | 128/202.21 |
| 2014/0378790 A1* | 12/2014 | Cohen | A61B 5/082 |
| | | | 600/300 |
| 2017/0143042 A1* | 5/2017 | Batista | H05B 3/26 |

FOREIGN PATENT DOCUMENTS

| | | |
|---|---|---|
| CN | 105249539 A | 1/2016 |
| EP | 0628376 A1 | 12/1994 |
| JP | H05-40102 A | 2/1993 |
| JP | H06-43128 A | 2/1994 |
| JP | 3418248 B2 | 6/2003 |
| JP | 2015-512262 A | 4/2015 |
| JP | 2015-532828 A | 11/2015 |
| WO | WO-2013/098398 A2 | 7/2013 |
| WO | WO-2015165813 A1 | 11/2015 |
| WO | WO-2016/005533 A1 | 1/2016 |
| WO | WO-2016/005601 A1 | 1/2016 |

OTHER PUBLICATIONS

International Search Report and Written Opinion for corresponding international application No. PCT/EP2017/057527 dated May 16, 2017.
International Prelimiminary Report on Patentability dated Mar. 28, 2018.
Russian Decision to Grant and Search Report for corresponding Application No. 2018140964, dated May 22, 2020.
First Office Action and Search Report issued on Sep. 27, 2020 in Chinese Application No. 201780020817.7.
Office Action dated Feb. 25, 2021 issued in corresponding Japanese Patent Application No. 2018-553090.
Japanese Office Action dated Aug. 2, 2021 for corresponding Japanese Application No. 2018-553090.
Korean Office Action dated Dec. 7, 2021 for corresponding Korean Application No. 10-2018-7030168, and English-language translation thereof.
Korean Notice of Allowance dated Jun. 23, 2022 for corresponding Korean Application No. 10-2018-7030168, and English-language translation thereof.

* cited by examiner

AEROSOL GENERATING DEVICE COMPRISING SEMICONDUCTOR HEATERS

This is a continuation of U.S. application Ser. No. 16/835,988, filed Mar. 31, 2020, which is a continuation of U.S. application Ser. No. 15/493,821, filed Apr. 21, 2017, which is a continuation of and claims priority to PCT/EP2017/057527 filed on Mar. 30, 2017, and further claims priority to EP 16166728.2 filed on Apr. 22, 2016, the entire contents of each of which are incorporated herein by reference.

BACKGROUND

At least one example embodiment relates to an aerosol-generating device comprising semiconductor heaters. The aerosol-generating device may be an electrically operated smoking system.

One type of aerosol-generating system is an electrically operated smoking system. Handheld electrically operated smoking systems may comprise an aerosol-generating device comprising a battery, control electronics, and an electric heater configured to heat an aerosol-generating article. The aerosol-generating article comprises an aerosol-generating substrate, such as a tobacco rod or a tobacco plug, and the heater contained within the aerosol-generating device is inserted into or around the aerosol-generating substrate when the aerosol-generating article is inserted into the aerosol-generating device. The aerosol-generating article may comprise a capsule containing an aerosol-generating substrate, such as loose tobacco.

It would be desirable to provide an aerosol-generating device having improved control over heating of an aerosol-generating article.

SUMMARY

At least one example embodiment relates to an aerosol-generating device.

In at least one example embodiment, an aerosol-generating device comprises an electrical power supply; a cavity structure configured to receive an aerosol-generating article; a plurality of semiconductor heaters positioned within the cavity structure, each of the plurality of semiconductor heaters including, a substrate layer, and a heating layer on the substrate layer, the heating layer being a continuous layer; and a controller configured to control a supply of electrical power from the electrical power supply to each of the plurality of semiconductor heaters.

In at least one example embodiment, each of the plurality of semiconductor heaters shares a same substrate layer. The heating layer of one of the plurality of semiconductor heaters is spaced apart from other heating layers of one of the plurality of semiconductor heaters. The heating layer of each of the plurality of semiconductor heaters is on the same substrate layer.

In at least one example embodiment, the heating layer of each of the plurality of semiconductor heaters has a convex polygonal shape.

In at least one example embodiment, each of the plurality of semiconductor heaters is on an internal surface of the cavity structure. The cavity structure comprises a planar wall. The plurality of semiconductor heaters is on the planar wall.

In at least one example embodiment, each of the semiconductor heaters is substantially planar. Each of the semiconductor heaters extends over a total area of less than 7 square millimetres.

In at least one example embodiment, the aerosol-generating device also includes at least one semiconductor gas sensor.

In at least one example embodiment, the heating layer of at least one of the semiconductor heaters is a combined heating and gas sensing layer. The controller is configured to measure an electrical resistance of the combined heating and gas sensing layer to determine an amount of at least one gas within the cavity structure. The controller is configured to simultaneously: control a supply of electrical power from the electrical power supply to the combined heating and gas sensing layer; and measure the electrical resistance of the combined heating and gas sensing layer to determine an amount of the at least one gas within the cavity structure.

In at least one example embodiment, the controller is configured to control the supply of electrical power to the combined heating and gas sensing layer in response to the determined amount of the at least one gas within the cavity structure.

In at least one example embodiment, the at least one semiconductor gas sensor comprises: a semiconductor gas sensor overlying a gas sensor heater. The gas sensor heater is one of the plurality of semiconductor heaters.

In at least one example embodiment, the controller is configured to simultaneously: control a supply of electrical power from the electrical power supply to the gas sensor heater to heat the semiconductor gas sensor; and measure the electrical resistance of the semiconductor gas sensor to determine an amount of at least one gas within the cavity structure.

In at least one example embodiment, the controller is configured to control the supply of electrical power to the gas sensor heater in response to the determined amount of the at least one gas within the cavity structure.

In at least one example embodiment, the at least one semiconductor gas sensor comprises: at least two semiconductor gas sensors. Each of the at least two semiconductor gas sensors is sensitive to different gases within the cavity structure.

In at least one example embodiment, the controller is configured to control the supply of electrical power from the electrical power supply to each of the plurality of semiconductor heaters sequentially.

BRIEF DESCRIPTION OF THE DRAWINGS

The invention is further described, by way of example only, with reference to the accompanying drawings in which.

DETAILED DESCRIPTION

Figure 1:
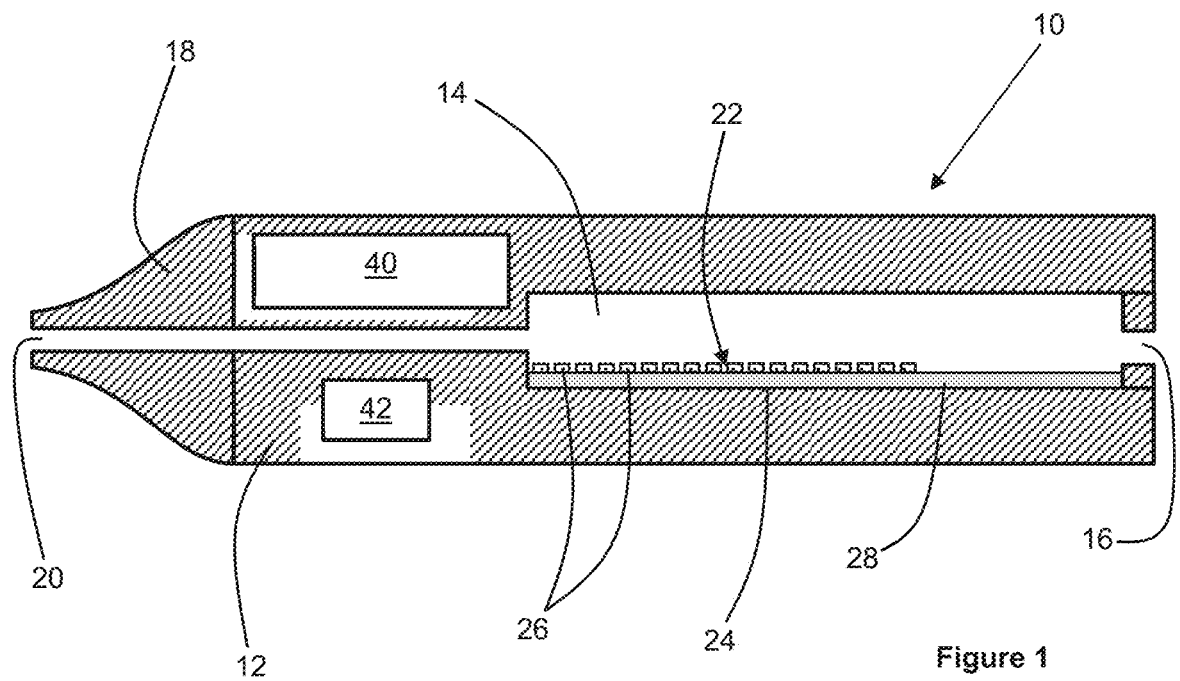
FIG. 1 is a cross-sectional view of an aerosol-generating device according to at least one example embodiment.

Various example embodiments will now be described more fully with reference to the accompanying drawings in which some example embodiments are shown. However, specific structural and functional details disclosed herein are merely representative for purposes of describing example embodiments. Thus, the embodiments may be embodied in many alternate forms and should not be construed as limited to only example embodiments set forth herein. Therefore, it should be understood that there is no intent to limit example embodiments to the particular forms disclosed, but on the contrary, example embodiments are to cover all modifications, equivalents, and alternatives falling within the scope.

In the drawings, the thicknesses of layers and regions may be exaggerated for clarity, and like numbers refer to like elements throughout the description of the figures.

Although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that, if an element is referred to as being "connected" or "coupled" to another element, it can be directly connected, or coupled, to the other element or intervening elements may be present. In contrast, if an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," if used herein, specify the presence of stated features, integers, steps, operations, elements and/or components, but do not preclude the presence or addition of one or more other features, integers, steps, operations, elements, components and/or groups thereof.

Spatially relative terms (e.g., "beneath," "below," "lower," "above," "upper" and the like) may be used herein for ease of description to describe one element or a relationship between a feature and another element or feature as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, for example, the term "below" can encompass both an orientation that is above, as well as, below. The device may be otherwise oriented (rotated 90 degrees or viewed or referenced at other orientations) and the spatially relative descriptors used herein should be interpreted accordingly.

Example embodiments are described herein with reference to cross-sectional illustrations that are schematic illustrations of idealized embodiments (and intermediate structures). As such, variations from the shapes of the illustrations as a result, for example, of manufacturing techniques and/or tolerances, may be expected. Thus, example embodiments should not be construed as limited to the particular shapes of regions illustrated herein but may include deviations in shapes that result, for example, from manufacturing. For example, an implanted region illustrated as a rectangle may have rounded or curved features and/or a gradient (e.g., of implant concentration) at its edges rather than an abrupt change from an implanted region to a non-implanted region. Likewise, a buried region formed by implantation may result in some implantation in the region between the buried region and the surface through which the implantation may take place. Thus, the regions illustrated in the figures are schematic in nature and their shapes do not necessarily illustrate the actual shape of a region of a device and do not limit the scope.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Although corresponding plan views and/or perspective views of some cross-sectional view(s) may not be shown, the cross-sectional view(s) of device structures illustrated herein provide support for a plurality of device structures that extend along two different directions as would be illustrated in a plan view, and/or in three different directions as would be illustrated in a perspective view. The two different directions may or may not be orthogonal to each other. The three different directions may include a third direction that may be orthogonal to the two different directions. The plurality of device structures may be integrated in a same electronic device. For example, when a device structure (e.g., a memory cell structure or a transistor structure) is illustrated in a cross-sectional view, an electronic device may include a plurality of the device structures (e.g., memory cell structures or transistor structures), as would be illustrated by a plan view of the electronic device. The plurality of device structures may be arranged in an array and/or in a two-dimensional pattern.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

As disclosed herein, the term "storage medium", "computer readable storage medium" or "non-transitory computer readable storage medium," may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Furthermore, at least some portions of example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, processor(s), processing circuit(s), or processing unit(s) may be programmed to perform the necessary tasks, thereby being transformed into special purpose processor(s) or computer(s).

A code segment may represent a procedure, function, subprogram, program, routine, subroutine, module, software package, class, or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded, or transmitted via any suitable means including memory sharing, message passing, token passing, network transmission, etc.

In order to more specifically describe example embodiments, various features will be described in detail with reference to the attached drawings. However, example embodiments described are not limited thereto.

At least one example embodiment relates to an aerosol-generating device.

In at least one example embodiment, an aerosol-generating device includes an electrical power supply, a cavity structure configured to receive an aerosol-generating article, and a plurality of semiconductor heaters within the cavity structure. Each of the plurality of semiconductor heaters comprises a substrate layer and a heating layer on the substrate layer. The heating layer is a continuous layer. The aerosol-generating device further comprises a controller configured to control a supply of electrical power from the electrical power supply to each of the semiconductor heaters.

The aerosol-generating device may comprise a plurality of semiconductor heaters positioned within a cavity structure, the cavity structure being configured to receive an aerosol-generating article. A plurality of semiconductor heaters may provide improved control over the heating of an aerosol-generating article received within the cavity structure. The temperature and duration of heating using each semiconductor heater may be accurately controlled when compared to other resistive heaters comprising a metallic or ceramic resistive heating element.

Providing each semiconductor heater with a continuous heating layer may simplify the manufacture of the aerosol-generating device as compared to other devices in which heating elements comprise a patterned electrically conductive layer.

A plurality of semiconductor heaters may facilitate heating of discrete portions of an aerosol-generating article, which may provide an improved release of aerosol from the aerosol-generating article. Heating discrete portions of an aerosol-generating article may facilitate an adult vaper vaping a first portion of the aerosol-generating article over a first time period and vaping a second portion of the aerosol-generating article over a later second time period.

Heating discrete portions of an aerosol-generating article with a plurality of semiconductor heaters may facilitate a more accurate estimation of the level of vaping of an aerosol-generating article.

A plurality of semiconductor heaters may be within the cavity structure with a geometric distribution that more closely matches the shape and size of a portion of an aerosol-generating article when compared to other aerosol-generating devices comprising metallic or ceramic resistive heating elements. Matching the geometric distribution of the plurality of semiconductor heaters to the shape and size of a portion of an aerosol-generating article may provide a more uniform heating of the aerosol-generating article. A more uniform heating of an aerosol-generating article may increase the total aerosol delivery from the aerosol-generating article.

Each of the plurality of semiconductor heaters may be on an internal surface of the cavity structure.

The cavity structure may comprise a substantially planar wall. The plurality of semiconductor heaters is on the substantially planar wall. Providing the plurality of semiconductor heaters on a substantially planar wall may facilitate heating of a substantially planar aerosol-generating article. Providing the semiconductor heaters on a substantially planar wall may simplify the manufacture of the aerosol-generating device.

Each of the semiconductor heaters is substantially planar. Providing substantially planar semiconductor heaters may simplify the manufacture of both the semiconductor heaters and the aerosol-generating device. Substantially planar semiconductor heaters may facilitate optimized contact between each semiconductor heater and a portion of an aerosol-generating article when the aerosol-generating article is received within the cavity structure.

Each of the semiconductor heaters comprises a substrate layer and a heating layer provided on the substrate layer. Each heating layer may be on a separate substrate layer. The plurality of semiconductor heaters may have a common substrate layer and a plurality of heating layers spaced apart from each other and each on the common substrate layer. Each heating layer forms a semiconductor heater. Using a common substrate layer may simplify the manufacture of the plurality of semiconductor heaters and the aerosol-generating device. A suitable material for forming the substrate layer is silicon. The substrate layer may be a silicon wafer.

Each heating layer may have a convex polygonal shape. That is, the shape of each heating layer may be such that no line segment between any two points on the boundary of the heating layer extends outside of the heating layer. Suitable shapes include circular, oval, elliptical, triangular, rectangular, square, pentagonal, and so forth.

Each heating layer may comprise polycrystalline silicon. Each heating layer may comprise one or more dopants to provide the polycrystalline silicon with a desired electrical resistance. A suitable dopant is phosphorous.

Each heating layer may be provided directly on the substrate layer, so that there are no intervening layers between the heating layer and the substrate layer.

Each semiconductor heater may further comprise one or more intermediate layers between the heating layer and the substrate layer. Each semiconductor heater may comprise an insulating layer positioned between the heating layer and the substrate layer. In at least one example embodiment in which the plurality of semiconductor heaters comprises a common substrate layer, the insulating layer may be a common insulating layer overlying the common substrate layer and underlying a plurality of heating layers. A suitable material for forming the insulating layer is silicon nitride.

Each semiconductor heater may comprise one or more electrodes electrically connected to the heating layer. Each electrode is formed from an electrically conductive material. Each electrode may be formed from at least one metal. The at least one metal may comprise copper, zinc, aluminium, silver, gold, platinum, and combinations thereof.

Each semiconductor heater may comprise a passivation layer provided on the heating layer. A passivation layer may reduce and/or substantially prevent oxidation of the heating layer during operation of the heater. A suitable material for forming the passivation layer is silicon dioxide.

Each of the semiconductor heaters may be configured to operate at a temperature ranging from about 200 degrees Celsius to about 400 degrees Celsius. Each of the semiconductor heaters may be configured to operate at a voltage ranging from about 3 volts to about 6 volts.

Each of the semiconductor heaters may extend over a total area of less than about 7 square millimetres. In example embodiments in which each of the semiconductor heaters comprises a heating layer and one or more electrical contacts provided on a common substrate layer or a common insulating layer, the heating layer and the one or more electrical contacts extends over a total area of less than about 7 square millimetres. Providing a plurality of semiconductor heaters each having a size of less than about 7 square millimetres may facilitate accurate heating of discrete portions of an aerosol-generating article.

Each of the semiconductor heaters may overlie a portion of the internal surface of the cavity structure. The surface area of each portion of the internal surface is less than about 7 square millimetres. Providing a plurality of semiconductor heaters each having a size of less than about 7 square millimetres may facilitate improved control over heating of an aerosol-generating article.

Each semiconductor heater may directly overlie a portion of the internal surface of the cavity structure having a surface area of less than about 7 square millimetres.

One or more intervening layers may be between each semiconductor heater and the internal surface of the cavity structure so that each semiconductor heater indirectly overlies a portion of the internal surface of the cavity structure having an area of less than about 7 square millimetres.

In example embodiments in which each semiconductor heater comprises a heating layer and one or more electrodes positioned on a common substrate layer, the heating layer and the one or electrodes may overlie a portion of the common substrate layer having a surface area of less than about 7 square millimetres. That is, the heating layer and the one or more electrodes indirectly overlie a portion of the internal surface of the cavity structure having a surface area of less than about 7 square millimetres.

In example embodiments in which each semiconductor heater comprises a heating layer and one or more electrodes positioned on a common insulating layer, the heating layer and the one or electrodes may overlie a portion of the common insulating layer having a surface area of less than about 7 square millimetres. That is, the heating layer and the one or more electrodes indirectly overlie a portion of the internal surface of the cavity structure having a surface area of less than about 7 square millimetres.

The aerosol-generating device may further comprise at least one gas sensor. The aerosol-generating device may comprise a plurality of gas sensors. A gas sensor may be used to monitor the operation of the aerosol-generating device. In at least one example embodiment, the presence of an oxidizing gas or a reducing gas may indicate the depletion of an aerosol-forming substrate from an aerosol-generating article being heated by the aerosol-generating device. The presence of an oxidizing gas or a reducing gas may indicate that an aerosol-generating article is being heated by the aerosol-generating device to a temperature that is higher than the operating temperature of the aerosol-generating article.

Each gas sensor may be a semiconductor gas sensor.

In at least one example embodiment, each semiconductor gas sensor is positioned proximate at least one of the semiconductor heaters. Positioning each gas sensor proximate at least one of the semiconductor heaters may reduce and/or eliminate the need to provide one or more additional heaters for heating each gas sensor during operation of the gas sensor. In at least one example embodiment, the controller is configured to activate each gas sensor when a semiconductor heater proximate the gas sensor is activated. The controller may be configured to monitor an amount of at least one gas using each activated semiconductor gas sensor. That is, the controller may monitor an amount of at least one gas within the cavity structure using each activated semiconductor gas sensor. The controller may be configured to control a supply of electrical power to the semiconductor heater proximate the activated semiconductor gas sensor in response to an amount of the at least one gas determined with the activated semiconductor gas sensor, or in response to a change in the amount of the at least one gas determined with the activated semiconductor gas sensor. In at least one example embodiment, the controller may be configured to reduce a supply of electrical power to the semiconductor heater proximate the activated semiconductor gas sensor when the determined amount of the at least one gas increases. The controller may be configured to deactivate the semiconductor heater proximate the activated semiconductor gas sensor when an amount of the at least one gas exceeds a predetermined threshold. The controller may be configured to monitor an electrical resistance or change of electrical resistance of the sensor. The electrical resistance or change of electrical resistance of the sensor is indicative of the presence of a reducing or oxidizing gas.

At least one semiconductor gas sensor may overlie one of the semiconductor heaters. That is, the semiconductor heater underlying the semiconductor gas sensor may be a gas sensor heater. The controller may be configured to control a supply of electrical power from the electrical power supply to the gas sensor heater to heat the semiconductor gas sensor. That is, the controller may be configured to control a supply of electrical power from the electrical power supply to the heating layer of the gas sensor heater. The controller may be configured to simultaneously measure the electrical resistance of the semiconductor gas sensor to determine an amount of at least one gas within the cavity structure. The controller may be configured to control the supply of electrical power to the gas sensor heater in response to the determined amount of the at least one gas within the cavity structure or a change in the determined amount of the at least one gas within the cavity structure. In at least one example embodiment, the controller may be configured to reduce the supply of electrical power to the gas sensor heater when the determined amount of the at least one gas increases. The controller may be configured to terminate the supply of electrical power to the gas sensor heater when the determined amount of the at least one gas within the cavity structure exceeds a desired (or, alternatively predetermined) threshold.

Each semiconductor gas sensor may be a metal-oxide gas sensor. In at least one example embodiment, the gas sensor is a N-type semiconductor gas sensor, and in particular a tin-oxide gas sensor. N-type semiconductor sensors decrease in electrical resistance in the presence of a reducing gas, such as carbon monoxide (CO) or ammonia, and increase in electrical resistance in the presence of oxidizing gas, such as oxygen, nitric oxide (NO), or nitrogen dioxide ($NO_2$). A P-type semiconductor gas sensor can also be used. P-type semiconductor gas sensors behave in the opposite manner, so they increase in electrical resistance in the presence of a reducing gas and decrease in electrical resistance in the presence of oxidizing gas.

At least one of the plurality of semiconductor heaters may be configured to function as the at least one gas sensor. The heating layer of at least one of the semiconductor heaters may be configured to function as a gas sensor. That is, the heating layer may function as a combined heating and gas sensing layer. The controller may be configured to measure at least one electrical property of the heating layer to determine the presence or absence of one or more gases. The controller may be configured to measure at least one electrical property of the heating layer to measure an amount of at least one gas. The controller may be configured to measure the electrical resistance of the heating layer. The controller may be configured to simultaneously: control a supply of electrical power from the electrical power supply to the combined heating and gas sensing layer to heat the combined heating and gas sensing layer; and measure the electrical resistance of the combined heating and gas sensing layer to determine an amount of the at least one gas within the cavity structure. The controller may be configured to control the supply of electrical power to the combined heating and gas sensing layer in response to the determined amount of the at least one gas within the cavity structure or a change in the determined amount of the at least one gas within the cavity structure. In at least one example embodiment, the controller may be configured to reduce the supply of electrical power to the combined heating and gas sensing layer when the determined amount of the at least one gas increases. The controller may be configured to terminate the supply of electrical power to the combined heating and gas sensing layer when the determined amount of the at least one gas within the cavity structure exceeds a desired (or, alternatively predetermined) threshold.

Each semiconductor heater configured to function as a gas sensor may comprise one or more first electrodes electrically connected to the heating layer for supplying electrical power from the electrical power supply to the heating layer for heating the heating layer. The one or more first electrodes may comprise at least two first electrodes. Each semiconductor heater configured to function as a gas sensor may comprise one or more second electrodes electrically connected to the heating layer for measurement of at least one electrical property of the heating layer by the controller. The one or more second electrodes may comprise at least two second electrodes.

Each gas sensor may be configured to operate at a temperature ranging from about 200 degrees Celsius to about 400 degrees Celsius. Gas sensors, such as semiconductor gas sensors, operate by virtue of a chemical reaction that takes place when the gas directly contacts the sensor. At temperatures ranging from about 200 degrees Celsius to about 400 degrees Celsius, the sensor is more sensitive because the chemical reaction rate is increased.

In example embodiments in which the aerosol-generating device comprises a plurality of gas sensors, at least two of the gas sensors may be configured to be sensitive to different gases. One sensor may be configured to detect reducing gases and another may be configured to detect oxidizing gases. Both gas sensors may be sensitive to reducing gases but may be differently tuned (by changing the composition, fabrication or doping of the gas sensing layer) to be particularly sensitive to different gases. For example, one gas sensor may be tuned to sense CO while another may be tuned to be sensitive to $NO_2$.

In at least one example embodiment, the controller is configured to sequentially activate and deactivate the plurality of semiconductor heaters. That is, the controller may be configured to control the supply of electrical power from the electrical power supply to each of the semiconductor heaters sequentially. The controller may be configured to activate and deactivate the plurality of semiconductor heaters one at a time. The controller may be configured to activate the plurality of semiconductor heaters in two or more groups, wherein all of the semiconductor heaters within a group are activated at the same time. The controller may be configured to activate the next heater or group of heaters after the previous heater or group of heaters has been activated but before the previous heater or group of heaters has been deactivated.

The electrical power supply may comprise a direct current (DC) source. In at least one example embodiment, the electrical power supply comprises a battery. The electrical power supply may comprise a Nickel-metal hydride battery, a Nickel cadmium battery, or a Lithium based battery, for example a Lithium-Cobalt, a Lithium-Iron-Phosphate or a Lithium-Polymer battery.

An aerosol-generating article may be received within the cavity structure of the aerosol-generating device so that the article and the device together form an aerosol-generating system. As described herein, providing an aerosol-generating device comprising a plurality of semiconductor heaters may facilitate providing the heaters in a geometric distribution that more closely matches the shape and size of a portion of an aerosol-generating article when compared to aerosol-generating devices comprising metallic or ceramic resistive heating elements.

According to at least one example embodiment, an aerosol-generating device comprises an electrical power supply, a cavity structure configured to receive an aerosol-generating article, and a plurality of semiconductor heaters within the cavity structure. The aerosol-generating device further comprises a controller configured to control a supply of electrical power from the electrical power supply to each of the semiconductor heaters.

Each of the semiconductor heaters may comprise a substrate layer and a heating layer on the substrate layer. Each heating layer may be a substantially continuous layer. Each heating layer may form a pattern on the substrate layer. Providing a heating layer that forms a pattern on the substrate layer may provide a desired (or, alternatively predetermined) temperature distribution across the semiconductor heater during operation of the heater.

In at least one example embodiment, aerosol-generating devices may comprise any of the features described herein with respect to the example embodiments.

In at least one example embodiment, an aerosol-generating system comprises an aerosol-generating article and an aerosol-generating device, in accordance with any of the embodiments described herein. The aerosol-generating article comprises at least one aerosol-forming substrate. The plurality of semiconductor heaters is configured to heat the at least one aerosol-forming substrate when the aerosol-generating article is received within the cavity structure.

The aerosol-generating article may comprise a base layer, wherein the at least one aerosol-forming substrate is positioned on a surface of the base layer. In example embodiments in which the plurality of semiconductor heaters are on a substantially planar wall of the cavity structure, the base layer is substantially planar.

The at least one aerosol-forming substrate may comprise an aerosol-forming substrate configured to overlie at least two of the semiconductor heaters when the aerosol-generating article is received within the cavity structure. The at least one aerosol-forming substrate may be a single aerosol-forming substrate configured to overlie all of the semiconductor heaters when the aerosol-generating article is received within the cavity structure.

The at least one aerosol-forming substrate may comprise a plurality of aerosol-forming substrates. Each aerosol-forming substrate is configured to overlie at least one of the semiconductor heaters when the aerosol-generating article is received within the cavity structure. The number of aerosol-forming substrates may be the same as the number of semiconductor heaters. Each aerosol-forming substrate is configured to overlie one of the semiconductor heaters when the aerosol-generating article is received within the cavity structure.

In example embodiments in which each of the semiconductor heaters overlies a portion of the internal surface of the cavity structure and the surface area of each portion of the internal surface is less than about 7 square millimetres, each of the aerosol-forming substrates is on a surface of the base layer. The surface area of each portion of the surface of the base layer is less than about 7 square millimetres. Providing a plurality of aerosol-forming substrates, each overlying a surface area of less than about 7 square millimetres, may facilitate uniform heating of each aerosol-forming substrate by the corresponding semiconductor heater.

According to at least one example embodiment, an aerosol-generating article comprises a base layer and a plurality of aerosol-forming substrates positioned on a surface of the base layer. Each aerosol-forming substrate overlies a portion of the surface of the base layer. The surface area of each portion of the surface of the base layer is less than about 7 square millimetres. The base layer is substantially planar.

In at least one example embodiment, the aerosol-generating article comprises a removable cover layer overlying and secured to the base layer so that the one or more aerosol-forming substrates are sealed between the removable cover layer and the base layer. The removable cover layer may comprise a non-porous polymeric film.

In example embodiments in which the aerosol-generating article comprises a plurality of aerosol-forming substrates, the plurality of aerosol-forming substrates may comprises a plurality of first aerosol-forming substrates on the base layer and a plurality of second aerosol-forming substrates on the base layer. The second aerosol-forming substrates are different from the first aerosol-forming substrates.

The controller may be configured to sequentially activate the plurality of semiconductor heaters so that the first aerosol-forming substrates are heated separately from the second aerosol-forming substrates. The controller may be configured to activate the plurality of semiconductor heaters so that at least some of the first aerosol-forming substrates are heated simultaneously with at least some of the second aerosol-forming substrates.

Both the first and second aerosol-forming substrates may each comprise a solid aerosol-forming substrate. Both the first and second aerosol-forming substrates may each comprise a liquid aerosol-forming substrate. Each of the first aerosol-forming substrates may comprise a solid aerosol-forming substrate and each of the second aerosol-forming substrates may comprise a liquid aerosol-forming substrate. Each of the first aerosol-forming substrates may comprise a liquid aerosol-forming substrate and each of the second aerosol-forming substrates may comprise a solid aerosol-forming substrate.

In example embodiments in which at least one of the first and second aerosol-forming substrates comprises a liquid aerosol-forming substrate, each of the aerosol-forming substrates may comprise a porous substrate material positioned on the base layer and the liquid aerosol-forming substrate sorbed onto the porous substrate material. In at least one example embodiment, the porous substrate material has a density of ranging from about 0.1 grams/cubic centimetre to about 0.3 grams/cubic centimetre.

In at least one example embodiment, the porous substrate material has a porosity ranging from about 15 percent to about 55 percent.

The porous substrate material may comprise one or more of glass, cellulose, ceramic, stainless steel, aluminium, polyethylene (PE), polypropylene, polyethylene terephthalate (PET), poly(cyclohexanedimethylene terephthalate) (PCT), polybutylene terephthalate (PBT), polytetrafluoroethylene (PTFE), expanded polytetrafluoroethylene (ePTFE), and BAREX®.

In at least one example embodiment, the porous substrate material is chemically inert with respect to the liquid aerosol-forming substrate.

In example embodiments comprising at least one solid aerosol-forming substrate, the solid aerosol-forming substrate may comprise tobacco. The solid aerosol-forming substrate may comprise a tobacco-containing material containing volatile tobacco flavour compounds which are released from the substrate upon heating. The solid aerosol-forming substrate may comprise a non-tobacco material. The solid aerosol-forming substrate may comprise tobacco-containing material and non-tobacco containing material.

The solid aerosol-forming substrate may include at least one aerosol-former. Suitable aerosol-formers include, but are not limited to: polyhydric alcohols, such as propylene glycol, triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate In at least one example embodiment, aerosol formers are polyhydric alcohols or mixtures thereof, such as propylene glycol, triethylene glycol, 1,3-butanediol, and glycerine.

In at least one example embodiment, the solid aerosol-forming substrate may comprise a single aerosol former. In at least one example embodiment, the solid aerosol-forming substrate may comprise a combination of two or more aerosol formers.

The solid aerosol-forming substrate may have an aerosol former content of greater than 5 percent on a dry weight basis.

The solid aerosol-forming substrate may have an aerosol former content ranging from about 5 percent to about 30 percent on a dry weight basis.

The solid aerosol-forming substrate may have an aerosol former content of about 20 percent on a dry weight basis.

In example embodiments comprising at least one liquid aerosol-forming substrate, the liquid aerosol-forming substrate may comprise a nicotine solution. The liquid aerosol-forming substrate comprises a tobacco-containing material comprising volatile tobacco flavor compounds which are released from the liquid upon heating. The liquid aerosol-forming substrate may comprise a non-tobacco material. The liquid aerosol-forming substrate may include water, solvents, ethanol, plant extracts and natural or artificial flavours. The liquid aerosol-forming substrate further comprises an aerosol former.

In example embodiments in which the aerosol-generating article comprises a plurality of first aerosol-forming substrates and a plurality of second aerosol-forming substrates, the plurality of first aerosol-forming substrates may each comprise a nicotine solution and the plurality of second aerosol-forming substrates may each comprise an acid.

The acid may comprise an organic acid or an inorganic acid.

In at least one example embodiment, the acid comprises an organic acid. In at least one example embodiment, the acid comprises a carboxylic acid. In at least one example embodiment, the acid comprises an alpha-keto or 2-oxo acid or lactic acid.

In at least one example embodiment, the acid comprises an acid selected from the group consisting of 3-methyl-2-oxopentanoic acid, pyruvic acid, 2-oxopentanoic acid, 4-methyl-2-oxopentanoic acid, 3-methyl-2-oxobutanoic acid, 2-oxooctanoic acid, lactic acid and combinations thereof. In at least one example embodiment, the acid comprises pyruvic acid or lactic acid. In at least one example embodiment, the acid comprises lactic acid.

In example embodiments in which the aerosol-generating article comprises a plurality of first aerosol-forming substrates each comprises a nicotine solution and a plurality of second aerosol-forming substrates each comprising an acid, the controller is configured to activate the plurality of semiconductor heaters so that at least some of the first aerosol-forming substrates are heated simultaneously with at least some of the second aerosol-forming substrates. Simultaneously heating the liquid nicotine solution and the acid may generate a nicotine aerosol and an acid aerosol that react in the gas phase to form an aerosol comprising nicotine salt particles.

At least one of the aerosol-forming substrates may comprise a flavorant. Suitable flavorants include, but are not limited to, menthol.

FIG. 1 is a cross-sectional view of an aerosol-generating device 10 according to at least one example embodiment.

In at least one example embodiment, as shown in FIG. 1, the aerosol-generating device 10 comprises a housing 12 (or cavity structure) defining a cavity 14 for receiving an aerosol-generating article. An air inlet 16 is provided at an upstream end of the cavity 14 and a mouthpiece 18 is provided at a downstream end of the housing 12. An air outlet 20 is provided in the mouthpiece 18 in fluid communication with the cavity 14 so that an airflow path is defined through the cavity 14 between the air inlet 16 and the air outlet 20. A draw on the mouthpiece 18 draws air into the cavity 14 through the air inlet 16 and out of the cavity 14 through the air outlet 20.

Figure 2:
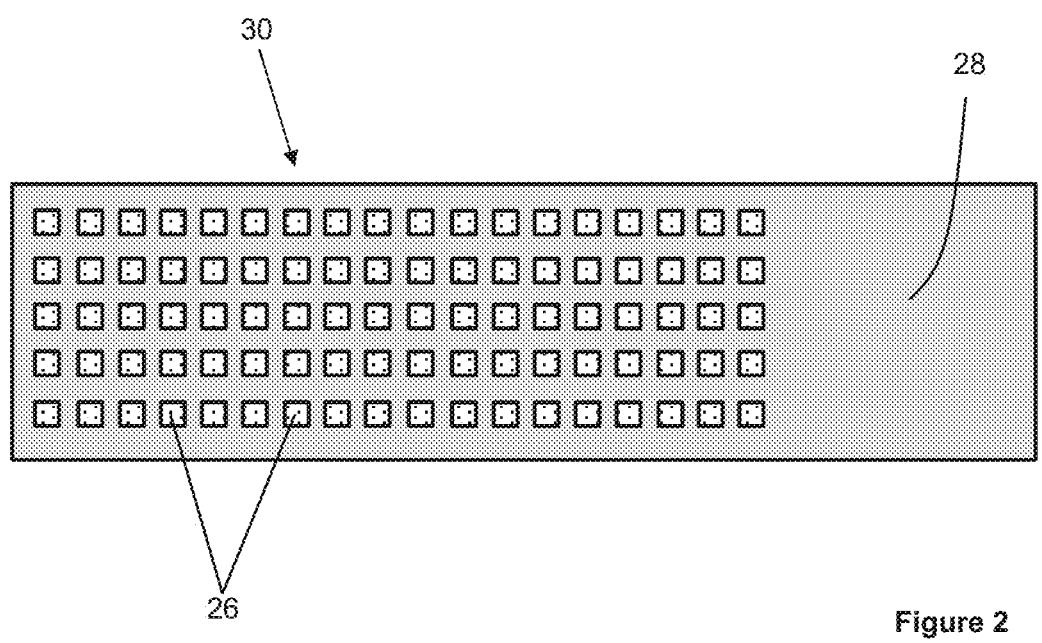
FIG. 2 is a top view of a plurality of semiconductor heaters of the aerosol-generating device of FIG. 1 according to at least one example embodiment.

The aerosol-generating device 10 further comprises a plurality of semiconductor heaters 22 provided on a planar wall 24 of the cavity 14. Each of the semiconductor heaters 22 comprises a heater package 26 on a common support layer 28. The plurality of semiconductor heaters 22 form a heater array 30, which is shown more clearly in FIG. 2.

Figure 3:
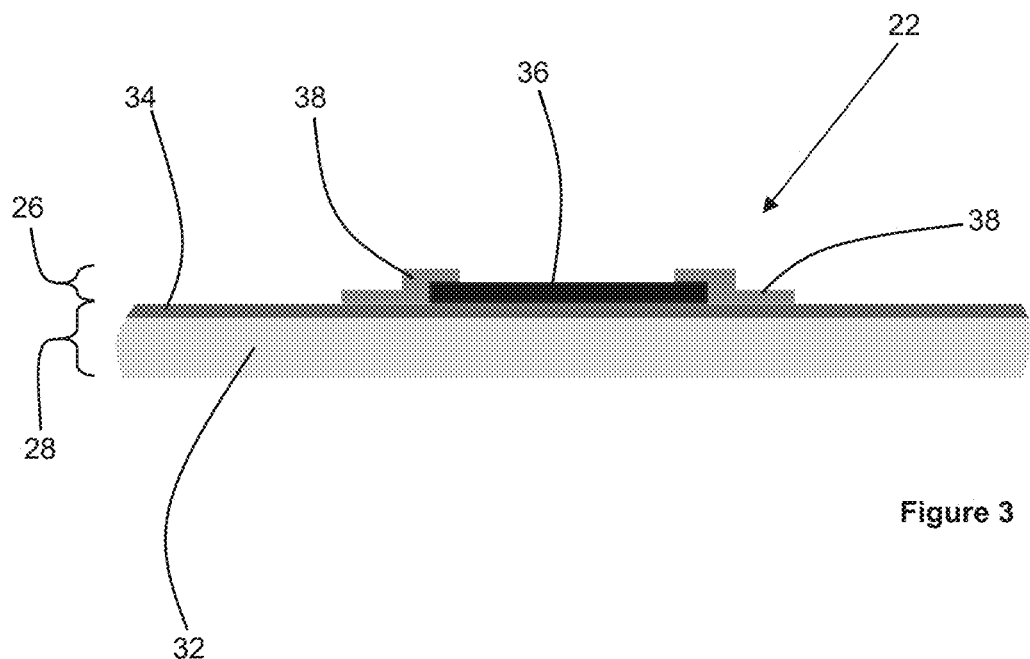
FIG. 3 is a detailed cross-sectional view of one of the semiconductor heaters of the aerosol-generating device of FIG. 1 according to at least one example embodiment.

FIG. 3 shows a cross-sectional view of an individual semiconductor heater 22. Each semiconductor heater 22 comprises a heater package 26 provided on a common support layer 28. The common support layer 28 comprises a common substrate layer 32 and a common insulating layer 34 overlying the common substrate layer 32. The common substrate layer 32 is a silicon wafer and the common insulating layer comprises silicon nitride.

Each heater package 26 comprises a heating layer 36 overlying a portion of the common insulating layer 34 and at least two electrodes 38 electrically connected to the heating layer 36. Each heater package 26 overlies a portion of the common insulating layer 34 have a surface area of less than about 7 square millimetres. The heating layer 36 comprises polycrystalline silicone doped with phosphorous to provide the heating layer 36 with a desired electrical resistance. The electrodes 38 comprise a metal, such as platinum.

In at least one example embodiment, as shown in FIG. 1, the aerosol-generating device 10 further comprises an electrical power supply 40 and a controller 42 positioned within the housing 12. During operation of the aerosol-generating device 10, the controller 42 controls a supply of electrical current from the electrical power supply 40 to each semiconductor heater 22 via the corresponding electrodes 38 to activate the semiconductor heater 22. The controller 42 is configured to activate the plurality of semiconductor heaters 22 in groups, with each group being activated and deactivated sequentially.

In at least one example embodiment, the controller 42 is further configured to measure and monitor the electrical resistance of the heating layer 36 of each semiconductor heater 22 when the heater is activated to measure and monitor an amount of at least one gas. In this way, each semiconductor heater 22 also functions as a gas sensor. In at least one example embodiment, each heating layer 36 may be sensitive to a gas that is generated when an aerosol-forming substrate on an aerosol-generating article is heated to a temperature above the operating temperature of the aerosol-generating article. In this scenario, the controller may be configured to deactivate the semiconductor heater 22 when the measured electrical resistance of the heating layer 36 of the semiconductor heater 22 is indicative of the presence of the gas.

Figure 4:
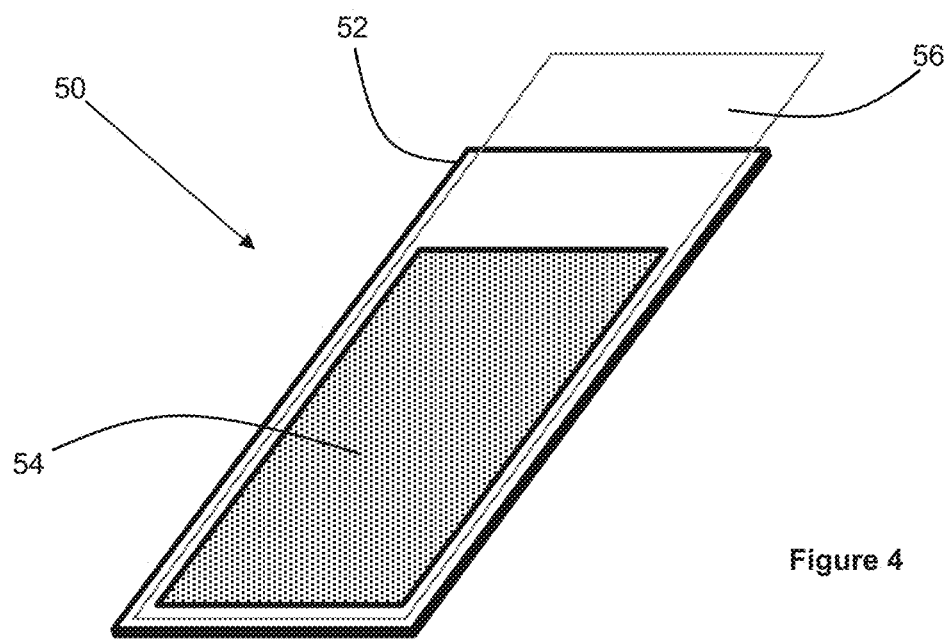
FIG. 4 is a perspective view of an aerosol-generating article according to at least one example embodiment.

FIG. 4 is an aerosol-generating article according to at least one example embodiment.

In at least one example embodiment, an aerosol-generating article 50 comprises a base layer 52 and an aerosol-forming substrate 54 on the base layer 52. The aerosol-forming substrate 54 comprises a substantially continuous layer of a solid tobacco-containing material. A removable cover layer 56 is secured to the base layer 52 to seal the aerosol-forming substrate 54 between the base layer 52 and the removable cover layer 56. The removable cover layer is formed from a non-porous polymeric film.

During operation, the removable cover layer 56 is removed from the base layer 52 and the aerosol-generating article 50 is inserted into the cavity 14 of the aerosol-generating device 10 shown in FIG. 1 to form an aerosol-generating system. The controller 42 then sequentially activates and deactivates groups of the semiconductor heaters 22 to sequentially heat discrete portions of the aerosol-forming substrate 54.

Figure 5:
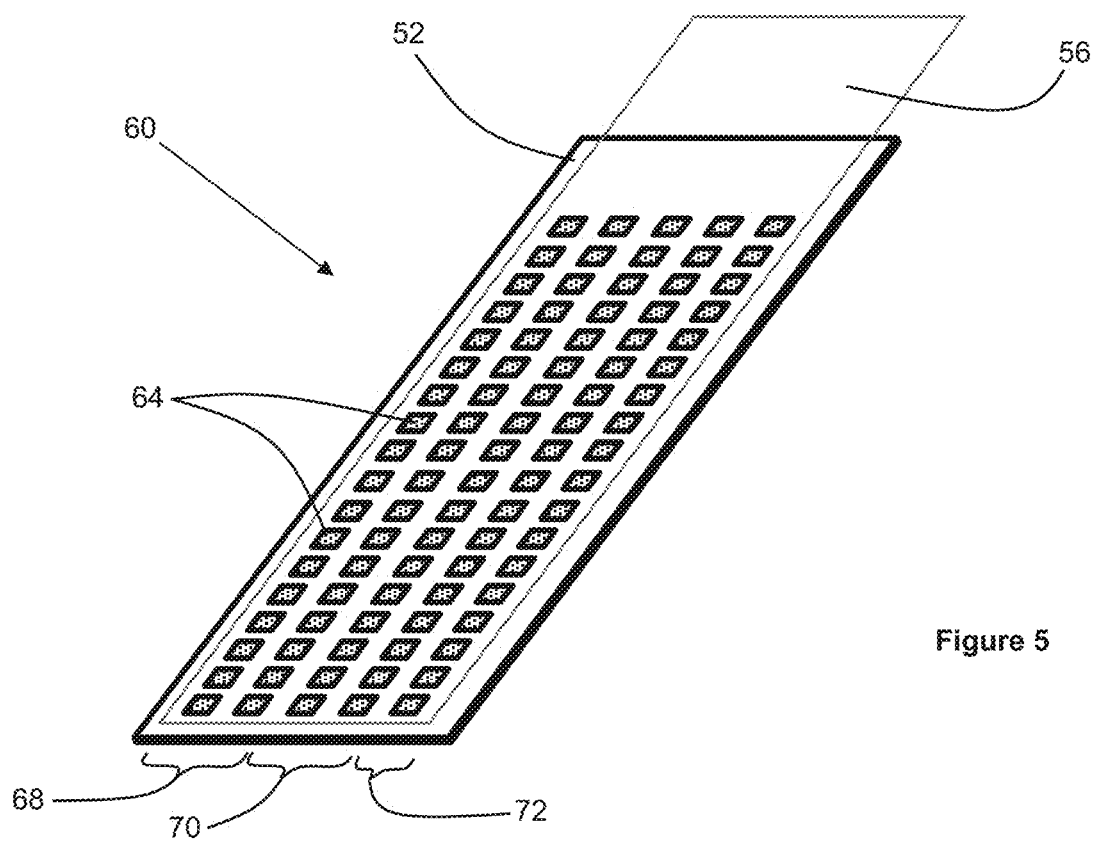
FIG. 5 is a perspective view of an aerosol-generating article according to at least one example embodiment.

FIG. 5 shows an aerosol-generating article 60 according to at least one example embodiment.

In at least one example embodiment, the aerosol-generating article 60 comprises a base layer 52 and a cover layer 56 identical to the base layer 52 and the cover layer 56 of the aerosol-generating article 50 shown in FIG. 4. However, the aerosol-generating article 60 comprises a plurality of discrete aerosol-forming substrates 64 positioned on the base layer 52 and sealed between the base layer 52 and the cover layer 56. Each of the aerosol-forming substrates 64 comprises a porous substrate material and a liquid aerosol-forming substrate sorbed onto the porous substrate material. Each of the aerosol-forming substrates 64 overlies a portion of the base layer 52 having a surface area of less than about 7 square millimetres.

The plurality of aerosol-forming substrates 64 is divided into three groups: a plurality of first aerosol-forming substrates 68 each comprising a liquid nicotine solution; a plurality of second aerosol-forming substrates 70 each comprising a volatile acid; and a plurality of third aerosol-forming substrates 72 each comprising a flavorant.

Figure 6:
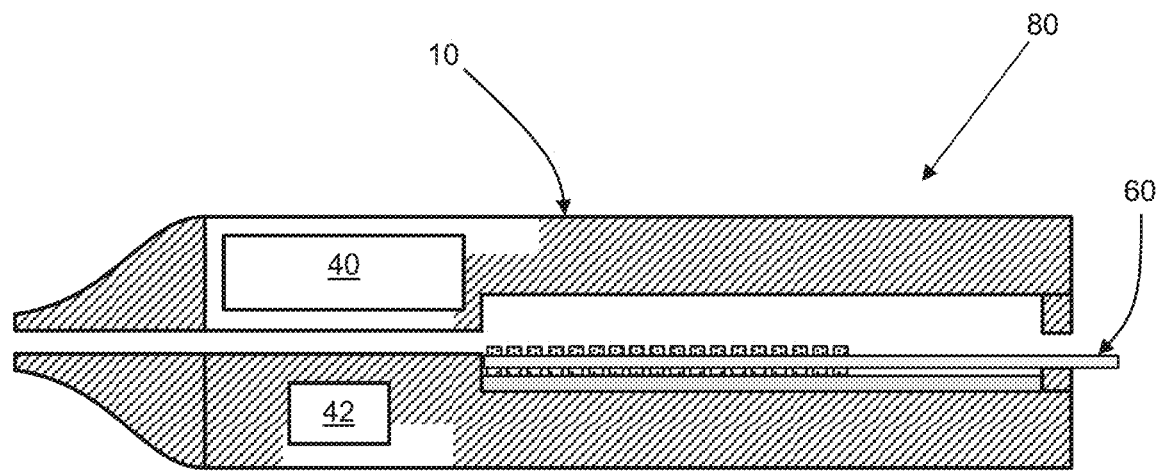
FIG. 6 is a cross-sectional view of the aerosol-generating article of FIG. 5 combined with the aerosol-generating device of FIG. 1 to form an aerosol-generating system according to at least one example embodiment.

During operation, the removable cover layer 56 is removed from the base layer 52 and the aerosol-generating article 60 is inserted into the cavity 14 of the aerosol-generating device 10 shown in FIG. 1 to form an aerosol-generating system 80, as shown in FIG. 6. The arrangement of the aerosol-forming substrates 64 is such that each aerosol-forming substrate 64 overlies a semiconductor heater 22 when the aerosol-generating article 60 is received within the cavity 14.

The controller 42 then sequentially activates and deactivates groups of the semiconductor heaters 22 to sequentially heat the discrete aerosol-forming substrates 64. At each stage of the sequential activation, the controller 42 activates the appropriate semiconductor heaters 22 to simultaneously heat one of the first aerosol-forming substrates 68, one of the second aerosol-forming substrates 70 and one of the third aerosol-forming substrates 72. The nicotine vapor released from the heated first aerosol-forming substrate 68 and the acid vapor released from the heated second aerosol-forming substrate 70 react in the gas phase to form an aerosol comprising nicotine salt particles for delivery through the air outlet 20. The flavorant released from the heated third aerosol-forming substrate 72 imparts a flavor to the aerosol.

It will be appreciated that features described for one example embodiment may be provided in other example embodiments.

I claim:

1. An aerosol-generating device comprising:
   a housing defining a cavity, the cavity configured to receive an aerosol-generating article;
   an electrical power supply in the housing;
   a plurality of semiconductor heaters in the cavity, each of the plurality of semiconductor heater including,
      a substrate layer, and
      a heating layer on the substrate layer, the heating layer of at least one of the plurality of semiconductor heaters including a semiconductor gas sensor such that the heating layer is a combined heating and gas sensing layer; and
   a controller configured to control a supply of electrical power from the electrical power supply to each of the plurality of semiconductor heaters, the controller configured to determine an amount of at least one gas within the cavity based on a measured electrical resistance of the combined heating and gas sensing layer, and
   wherein the controller is configured to simultaneously:
      control a supply of electrical power from the electrical power supply to the combined heating and gas sensing layer so as to heat the semiconductor gas sensor; and
      determine an amount of at least one gas within the cavity based on a measured electrical resistance of the combined heating and gas sensing layer.

2. The aerosol-generating device of claim 1, wherein the controller is configured to control the supply of electrical power to the combined heating and gas sensing layer in response to a determined amount of the at least one gas within the cavity.

3. The aerosol-generating device according to claim 1, wherein the substrate layer is a common substrate layer, and the heating layers of the plurality of semiconductor heaters are spaced apart from each other and on the common substrate layer.

4. The aerosol-generating device according to claim 1, wherein the heating layer of each of the plurality of semiconductor heaters has a convex polygonal shape.

5. The aerosol-generating device according to claim 1, wherein each of the plurality of semiconductor heaters is on an internal surface of the cavity.

6. The aerosol-generating device according to claim 1, wherein the cavity comprises:
   a planar wall, and
   the plurality of semiconductor heaters are on the planar wall.

7. The aerosol-generating device according to claim 1, wherein each of the plurality of semiconductor heaters is substantially planar.

8. The aerosol-generating device according to claim 1, wherein each of the plurality of semiconductor heaters extends over a total area of less than 7 square millimeters.

9. The aerosol-generating device according to claim 1, wherein the controller is configured to control the supply of electrical power from the electrical power supply to each of the plurality of semiconductor heaters sequentially.

10. The aerosol-generating device according to claim 1, wherein the aerosol-generating article comprises:
    a base layer, and
    a cover layer.

11. The aerosol-generating device according to claim 10, wherein the aerosol-generating article further comprises:
    a plurality of portions of an aerosol-forming substrates between the base layer and the cover layer.

12. The aerosol-generating device according to claim 11, wherein each of the plurality of portions include a porous substrate material and a liquid sorbed onto the porous substrate material.

13. The aerosol-generating device according to claim 11, wherein each of the plurality of portions include tobacco.

14. The aerosol-generating device according to claim 1, wherein the substrate layer comprises a silicon wafer.

15. The aerosol-generating device according to claim 14, wherein the heating layer comprises polycrystalline doped with phosphorous.

* * * * *